United States Patent
Sawalhe et al.

(10) Patent No.: US 10,016,214 B2
(45) Date of Patent: Jul. 10, 2018

(54) ACCESS SYSTEM FOR ENDOSCOPIC OPERATIONS

(71) Applicant: Karl Storz SE & Co. KG, Tuttlingen (DE)

(72) Inventors: Samir Sawalhe, Deggendorf (DE); Rainer Hermle, Gosheim (DE); Frank Doll, Talheim (DE); Stefan Rehbein, Immendingen-Hattingen (DE); Alexander Haffa, Dauchingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 0 days.

(21) Appl. No.: 15/202,657

(22) Filed: Jul. 6, 2016

(65) Prior Publication Data

US 2017/0100160 A1    Apr. 13, 2017

(30) Foreign Application Priority Data

Oct. 8, 2015    (DE) .................... 10 2015 012 964

(51) Int. Cl.
*A61B 1/32*    (2006.01)
*A61B 17/34*    (2006.01)
(Continued)

(52) U.S. Cl.
CPC .... *A61B 17/3423* (2013.01); *A61B 17/00234* (2013.01); *A61B 17/0218* (2013.01);
(Continued)

(58) Field of Classification Search
CPC ............ A61B 17/3423; A61B 17/0218; A61B 17/3421; A61B 2017/0225;
(Continued)

(56) References Cited

U.S. PATENT DOCUMENTS 3,039,468 A * 6/1962 Price .................. A61D 1/14
604/107
3,717,151 A * 2/1973 Collett .................. A61M 25/02
604/106

(Continued)

FOREIGN PATENT DOCUMENTS

DE    8216373 U1    7/1982
DE    19624826 A1    1/1998
(Continued)

OTHER PUBLICATIONS

German Search Report Application No. 10201501294.3 dated Jun. 28, 2016 10 pages.

*Primary Examiner* — Eduardo C Robert
*Assistant Examiner* — Michelle C Eckman
(74) *Attorney, Agent, or Firm* — Whitmyer IP Group LLC

(57) ABSTRACT

An access system for endoscopic operations includes of a trocar, a cover that is fittable on the trocar and at least one spreading element having a retaining portion and an effector portion, wherein the access system has, between the trocar and the cover in the fitted state, a receiving region for the retaining portion of the at least one spreading element. Furthermore, the access system can include an extraction bag which is expanded by the effector portion of the at least one spreading element.

13 Claims, 5 Drawing Sheets

US 10,016,214 B2

Page 2

(51) Int. Cl.
    *A61B 17/00* (2006.01)
    *A61B 17/02* (2006.01)
    *A61B 17/32* (2006.01)
(52) U.S. Cl.
    CPC ...... *A61B 17/3421* (2013.01); *A61B 17/3439* (2013.01); *A61B 2017/00287* (2013.01); *A61B 2017/320024* (2013.01)
(58) Field of Classification Search
    CPC ... A61B 17/3439; A61B 17/3462; A61B 1/32; A61B 17/3417; A61B 2017/3484; A61B 2017/3419; A61B 2017/3429; A61B 17/02
    See application file for complete search history.

(56) References Cited

U.S. PATENT DOCUMENTS

| | | | | |
|---|---|---|---|---|
| 3,902,501 | A * | 9/1975 | Citron | A61N 1/057 607/126 |
| 4,043,346 | A * | 8/1977 | Mobley | A61M 25/04 604/107 |
| 5,330,501 | A * | 7/1994 | Tovey | A61B 17/3421 604/105 |
| 5,370,647 | A * | 12/1994 | Graber | A61B 17/00234 606/127 |
| 5,443,484 | A * | 8/1995 | Kirsch | A61B 17/0281 604/164.04 |
| 5,577,993 | A * | 11/1996 | Zhu | A61B 17/0281 600/204 |
| 5,690,606 | A | 11/1997 | Slotman | |
| 5,707,359 | A * | 1/1998 | Bufalini | A61B 17/3421 604/104 |
| 6,027,518 | A * | 2/2000 | Gaber | A61B 17/22031 604/105 |
| 6,383,195 | B1 * | 5/2002 | Richard | A61B 17/221 606/114 |
| 6,482,178 | B1 * | 11/2002 | Andrews | A61B 90/92 604/104 |
| 7,052,502 | B2 | 5/2006 | Le Huec et al. | |
| 8,157,833 | B2 * | 4/2012 | Au | A61B 17/34 606/105 |
| 8,360,969 | B2 * | 1/2013 | Hanypsiak | A61B 17/3421 600/184 |
| 8,795,326 | B2 * | 8/2014 | Richard | A61B 17/3423 600/206 |
| 9,717,399 | B2 * | 8/2017 | Newman | A61B 1/05 |
| 2002/0038128 | A1 * | 3/2002 | Turovkiy | A61B 17/3417 606/164 |
| 2002/0137988 | A1 * | 9/2002 | Shipp | A61B 17/00234 600/204 |
| 2003/0009185 | A1 * | 1/2003 | Jessen | A61B 17/32093 606/167 |
| 2003/0023201 | A1 * | 1/2003 | Aboul-Hosn | A61B 17/3421 604/19 |
| 2003/0032975 | A1 * | 2/2003 | Bonutti | A61B 17/0218 606/192 |
| 2003/0199915 | A1 * | 10/2003 | Shimm | A61B 17/3439 606/198 |
| 2003/0208153 | A1 * | 11/2003 | Stenzel | A61B 17/29 604/60 |
| 2003/0216773 | A1 * | 11/2003 | Shimm | A61B 17/3439 606/198 |
| 2004/0127913 | A1 * | 7/2004 | Voss | A61B 17/0057 606/108 |
| 2004/0173218 | A1 * | 9/2004 | Yamada | A61B 17/0293 128/856 |
| 2004/0225192 | A1 * | 11/2004 | Young | A61B 17/34 600/204 |
| 2005/0043682 | A1 * | 2/2005 | Kucklick | A61B 17/3421 604/164.09 |
| 2005/0049624 | A1 * | 3/2005 | Francese | A61B 17/3421 606/185 |
| 2005/0085771 | A1 * | 4/2005 | Lyon | A61B 17/3421 604/107 |
| 2005/0119652 | A1 * | 6/2005 | Vetter | A61B 10/0041 606/45 |
| 2005/0119685 | A1 * | 6/2005 | Smith | A61B 17/3439 606/198 |
| 2005/0159711 | A1 * | 7/2005 | Kathrani | A61B 17/34 604/264 |
| 2005/0216028 | A1 * | 9/2005 | Hart | A61B 17/3498 606/108 |
| 2006/0025781 | A1 * | 2/2006 | Young | A61B 17/0218 606/114 |
| 2006/0089662 | A1 * | 4/2006 | Davison | A61B 17/0218 606/198 |
| 2006/0095054 | A1 * | 5/2006 | Zannis | A61B 17/0401 606/148 |
| 2006/0106415 | A1 * | 5/2006 | Gabbay | A61B 17/3468 606/198 |
| 2006/0129165 | A1 * | 6/2006 | Edoga | A61B 17/34 606/108 |
| 2006/0142642 | A1 * | 6/2006 | Lins | A61B 1/32 600/210 |
| 2006/0167487 | A1 * | 7/2006 | Hamada | A61B 17/02 606/198 |
| 2006/0178675 | A1 * | 8/2006 | Hamman | A61B 17/34 606/108 |
| 2006/0200186 | A1 * | 9/2006 | Marchek | A61B 17/0218 606/191 |
| 2006/0206008 | A1 * | 9/2006 | Dalton | A61B 17/0218 600/215 |
| 2006/0229636 | A1 * | 10/2006 | Woodburn, Sr. | A61B 17/02 606/108 |
| 2006/0235279 | A1 * | 10/2006 | Hawkes | A61B 1/32 600/222 |
| 2007/0005086 | A1 * | 1/2007 | Gresham | A61B 17/3417 606/167 |
| 2007/0010715 | A1 * | 1/2007 | Sixto, Jr. | A61B 17/0218 600/217 |
| 2007/0073112 | A1 * | 3/2007 | Holmes | A61B 17/02 600/225 |
| 2007/0149845 | A1 * | 6/2007 | Kuhns | A61B 1/00085 600/101 |
| 2007/0162066 | A1 * | 7/2007 | Lyon | A61B 17/3421 606/191 |
| 2007/0198045 | A1 * | 8/2007 | Morton | A61B 17/3439 606/191 |
| 2007/0219416 | A1 * | 9/2007 | Perez-Cruet | A61B 17/02 600/219 |
| 2007/0276370 | A1 * | 11/2007 | Altarac | A61B 17/0206 606/86 A |
| 2008/0021552 | A1 * | 1/2008 | Gabbay | A61B 17/3421 623/11.11 |
| 2008/0058590 | A1 * | 3/2008 | Saadat | A61B 1/00085 600/109 |
| 2008/0108875 | A1 * | 5/2008 | Kunkel | A61B 17/34 600/204 |
| 2008/0132946 | A1 * | 6/2008 | Mueller | A61B 17/3417 606/232 |
| 2008/0161644 | A1 * | 7/2008 | Ghabrial | A61B 1/00135 600/114 |
| 2008/0172009 | A1 * | 7/2008 | Attinger | A61F 9/00736 604/264 |
| 2008/0177288 | A1 * | 7/2008 | Carlson | A61B 17/0057 606/144 |
| 2008/0269557 | A1 * | 10/2008 | Marescaux | A61B 1/018 600/106 |
| 2008/0287988 | A1 * | 11/2008 | Smith | A61B 17/0057 606/216 |
| 2008/0319261 | A1 * | 12/2008 | Lucini | A61B 17/3421 600/114 |
| 2009/0023975 | A1 * | 1/2009 | Marseille | A61B 17/3421 600/16 |
| 2009/0030443 | A1 * | 1/2009 | Buser | A61B 17/3423 606/185 |
| 2009/0082802 | A1 * | 3/2009 | Benjamin | A61B 17/0057 606/213 |

(56) References Cited

U.S. PATENT DOCUMENTS

| | | | |
|---|---|---|---|
| 2009/0264703 A1* | 10/2009 | Pribanic | A61B 1/0008 600/121 |
| 2009/0275802 A1* | 11/2009 | Hawkes | A61B 17/0218 600/219 |
| 2009/0306586 A1* | 12/2009 | Ross | A61B 17/3439 604/93.01 |
| 2010/0010449 A1* | 1/2010 | Leibowitz | A61B 17/3421 604/179 |
| 2010/0069947 A1* | 3/2010 | Sholev | A61B 17/00234 606/192 |
| 2010/0191296 A1* | 7/2010 | Lyon | A61B 17/3417 606/86 R |
| 2010/0198159 A1* | 8/2010 | Voss | A61B 17/0057 604/171 |
| 2010/0240959 A1* | 9/2010 | Donahue | A61B 17/3421 600/204 |
| 2010/0249517 A1* | 9/2010 | Fischvogt | A61B 17/3421 600/204 |
| 2010/0298857 A1* | 11/2010 | Zook | A61B 17/3403 606/185 |
| 2010/0305407 A1* | 12/2010 | Farley | A61B 17/0206 600/206 |
| 2011/0021879 A1* | 1/2011 | Hart | A61B 17/0293 600/207 |
| 2011/0034775 A1* | 2/2011 | Lozman | A61B 17/1684 600/204 |
| 2011/0034776 A1* | 2/2011 | Dixon | A61B 1/303 600/205 |
| 2011/0040154 A1* | 2/2011 | Reznik | A61B 17/3421 600/227 |
| 2011/0082339 A1* | 4/2011 | Elliott, III | A61B 17/0281 600/204 |
| 2011/0144437 A1* | 6/2011 | Ortiz | A61B 17/3421 600/201 |
| 2011/0144440 A1* | 6/2011 | Cropper | A61B 17/3421 600/203 |
| 2011/0144447 A1* | 6/2011 | Schleitweiler | A61B 17/3421 600/210 |
| 2011/0144448 A1* | 6/2011 | Shelton, IV | A61B 17/3423 600/216 |
| 2011/0224678 A1* | 9/2011 | Gabbay | A61B 17/3468 606/108 |
| 2011/0224679 A1* | 9/2011 | Fischvogt | A61B 17/3209 606/108 |
| 2011/0224742 A1* | 9/2011 | Weisel | A61B 17/0218 606/86 R |
| 2011/0306841 A1* | 12/2011 | Lozman | A61B 17/1684 600/204 |
| 2012/0022575 A1* | 1/2012 | Mire | A61B 5/4893 606/198 |
| 2012/0065589 A1* | 3/2012 | Worrel | A61B 17/3417 604/164.04 |
| 2012/0130183 A1* | 5/2012 | Barnes | A61B 17/3423 600/206 |
| 2012/0165611 A1* | 6/2012 | Warren | A61B 17/3421 600/204 |
| 2012/0203241 A1* | 8/2012 | Williamson, IV | A61B 10/06 606/114 |
| 2012/0310049 A1* | 12/2012 | Oberlaender | A61B 17/0206 600/219 |
| 2012/0323081 A1* | 12/2012 | Son | A61M 39/0247 600/215 |
| 2013/0018408 A1* | 1/2013 | Farley | A61B 17/0218 606/198 |
| 2013/0030457 A1* | 1/2013 | Tan | A61B 17/3421 606/185 |
| 2013/0041398 A1* | 2/2013 | Goddard | A61M 29/00 606/191 |
| 2013/0053776 A1* | 2/2013 | Shelton, IV | A61B 17/3421 604/164.04 |
| 2013/0053777 A1* | 2/2013 | Shelton, IV | A61B 17/3421 604/164.04 |
| 2013/0053778 A1* | 2/2013 | Shelton, IV | A61B 17/3421 604/164.04 |
| 2013/0053779 A1* | 2/2013 | Shelton, IV | A61B 17/3421 604/164.04 |
| 2013/0053782 A1* | 2/2013 | Shelton, IV | A61B 17/3421 604/167.03 |
| 2013/0102843 A1* | 4/2013 | Feuer | A61B 1/00087 600/109 |
| 2013/0103048 A1* | 4/2013 | Burg | A61B 90/11 606/129 |
| 2013/0150654 A1* | 6/2013 | Stanfield | A61M 1/10 600/16 |
| 2013/0165956 A1* | 6/2013 | Sherts | A61B 17/0482 606/148 |
| 2013/0225934 A1* | 8/2013 | Raybin | A61B 17/32056 600/214 |
| 2013/0245677 A1* | 9/2013 | Sargeant | A61F 15/002 606/213 |
| 2014/0046213 A1* | 2/2014 | Benbunan | A61B 5/15 600/576 |
| 2014/0051934 A1* | 2/2014 | Ma | A61B 17/0218 600/208 |
| 2014/0094655 A1* | 4/2014 | Newman | A61B 1/0008 600/109 |
| 2014/0114140 A1* | 4/2014 | Ellman | A61B 17/0206 600/249 |
| 2014/0148648 A1* | 5/2014 | Tycast | A61B 17/3423 600/202 |
| 2014/0275768 A1* | 9/2014 | Luttati | A61B 1/00096 600/104 |
| 2014/0288377 A1* | 9/2014 | Worrel | A61B 17/3417 600/208 |
| 2014/0364697 A1* | 12/2014 | Son | A61B 1/32 600/215 |
| 2015/0038794 A1* | 2/2015 | Pattison | A61B 17/3415 600/204 |
| 2015/0080664 A1* | 3/2015 | Kobayashi | A61B 17/3421 600/204 |
| 2015/0196321 A1* | 7/2015 | Gregory | A61M 1/1008 606/108 |
| 2015/0209078 A1* | 7/2015 | Nevler | A61B 17/3417 604/96.01 |
| 2015/0297260 A1* | 10/2015 | Kreuz | A61B 17/34 606/185 |
| 2015/0351794 A1* | 12/2015 | Mastri | A61B 17/34 600/204 |
| 2016/0038018 A1* | 2/2016 | Wilson | A61B 17/3421 600/114 |
| 2016/0045220 A1* | 2/2016 | Wachli | A61B 17/3423 600/204 |
| 2016/0100857 A1* | 4/2016 | Wachli | A61B 17/3439 600/204 |
| 2016/0106461 A1* | 4/2016 | Morris | A61F 9/00736 600/204 |
| 2016/0192828 A1* | 7/2016 | Sexton | A61B 1/00154 600/114 |
| 2016/0228148 A1* | 8/2016 | Ravikumar | A61B 17/29 |
| 2017/0079658 A1* | 3/2017 | Walters | A61B 17/068 |
| 2017/0119430 A1* | 5/2017 | Keshvari | A61B 17/3415 |
| 2017/0224321 A1* | 8/2017 | Kessler | A61B 17/00234 |

FOREIGN PATENT DOCUMENTS

| | | |
|---|---|---|
| DE | 19937043 C2 | 10/2003 |
| DE | 202011051747 U1 | 1/2012 |
| DE | 102011088337 A1 | 6/2013 |

* cited by examiner

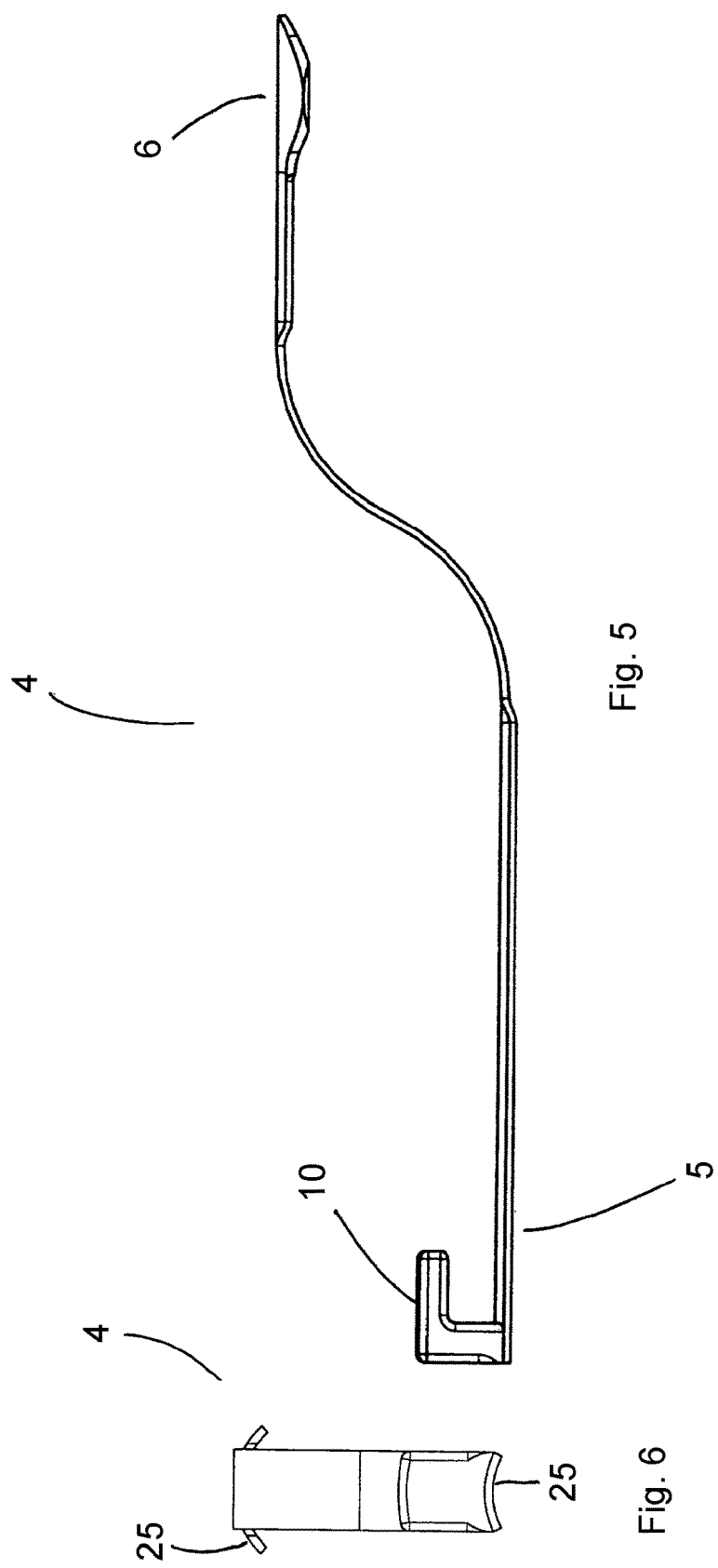

ACCESS SYSTEM FOR ENDOSCOPIC OPERATIONS

TECHNICAL FIELD

The present invention relates to an access system for endoscopic operations, having the possibility of expanding an extraction bag located in a body cavity in order for example to cut up the contents thereof by means of a morcellator and remove them from the body cavity.

BACKGROUND

Endoscopic operations for removing diseased tissue are known. To this end, an endoscope and one or more access means, for example trocars, are introduced into the body cavity in question and the affected tissue detached, for example by means of high-frequency surgery. If the pieces of tissue are small pieces of tissue, they can be removed from the body cavity through one of the access means. However, if the detached pieces of tissue are too large for removal through an access means, they have to be cut up prior to removal. This can be carried out for example by means of what is known as a morcellator, which has a rotating blade and a working duct passing through it. In this way, smaller pieces can be cut off large pieces of tissue and removed from the body cavity. In the case of infectious tissue, however, there is the risk of the disease spreading during the cutting up of the pieces of tissue, simply because tiny remnants of diseased tissue could remain in the body.

In order to prevent the spread of a disease, it is sensible to place a detached infectious piece of tissue in an extraction bag, also known as an endobag, to guide the open end of the latter through the access duct, and to morcellate the diseased piece of tissue in the extraction bag. This ensures that no remnants of infectious tissue remain in the body cavity. However, during endoscopic operations, body cavities are generally insufflated, i.e. a gas (nitrogen, carbon dioxide, helium etc.) is blown in in order to expand the body cavity. As a result, the surgeon is provided with more operating space.

However, as a result of the positive pressure within the body cavity, the extraction bag containing the detached diseased tissue is compressed so much that it is difficult if not impossible to detach the small pieces of tissue with the morcellator and remove them. In addition, there is the risk of the rotating blade of the morcellator cutting the extraction bag itself and parts of the infectious tissue passing back into the body cavity.

Therefore, the object of the invention can be considered that of specifying an access system for endoscopic operations, by way of which an extraction bag, in spite of the positive pressure in a body cavity, is expanded to such an extent that the tissue located in the extraction bag can be cut up without risk by means of a morcellator and removed.

This object is achieved by an access system for endoscopic operations according to independent claims 1, 8 and 13. Advantageous developments are the subject matter of the dependent claims.

SUMMARY

An access system for endoscopic operations consists of a trocar, a cover that is fittable on the trocar and at least one spreading element having a retaining portion and an effector portion, wherein the access system has, between the trocar and the cover in the fitted state, a receiving region for the retaining portion of the at least one spreading element. It is particularly advantageous with this configuration that the spreading element or, if present, several spreading elements is/are fittable individually on the trocar and yet are introducible without problems through the comparatively narrow access means.

In a further advantageous configuration, the trocar and the cover of the access system have a bayonet mount for fitting. In this way, the access system can be put together quickly and securely.

Furthermore, the receiving region of the access system can comprise an annular retaining ring.

Moreover, the retaining portion of the at least one spreading element can have a retaining clip adapted to the retaining ring.

Furthermore, the retaining ring can have at least one positioning portion adapted to the retaining clip of the at least one spreading element.

In a further configuration, the access system according to the invention can have 3 or 4 spreading elements. Depending on the specific embodiment, the access system according to the invention can also have 2 or 5 or 6 spreading elements, however.

In a further embodiment, the access system can comprise an extraction bag which is expanded by the effector portion of the at least one spreading element.

Moreover, the trocar can have a fluid feed. As a result, the extraction bag can be insufflated, i.e. blown up with nitrogen, carbon dioxide, helium or some other gas, independently of the body cavity, in order to build up a counterpressure to the insufflated body cavity. The expansion of the extraction bag is supported as a result. In this case, the insufflation gas can be fed via a distribution valve such that the insufflation pressure in the body cavity and in the extraction bag is maintained at the same or at least similar level.

A further embodiment of the access system according to the invention for endoscopic operations can consist of a trocar having a trocar sleeve, a cover that is fittable on the trocar and has a working duct and at least one spreading element, wherein the working duct extends concentrically within the trocar sleeve in the fitted state. The features of this embodiment can be used independently of the abovementioned embodiments or be combined with the abovementioned embodiment.

In a further embodiment, at least one portion of the at least one spreading element can extend within an intermediate space between the trocar sleeve and working duct. If the spreading elements have a flat or at least approximately flat cross section, this arrangement allows the precise orientation of the spreading elements around the trocar sleeve.

Furthermore, the at least one spreading element can have, at least in portions, a circular cylindrical contour which is adapted to the contour of the trocar sleeve and/or of the working duct. To this end, it is particularly advantageous for the portion in question of the spreading element to have a contour in the form of a circular cylindrical jacket, such that it bears as extensively as possible against the outer side of the working duct and against the inner side of the trocar sleeve.

The present embodiment of the access system according to the invention can also advantageously have 3 or 4, in particular cases also 2 or 5 or 6 spreading elements.

Likewise, the present configuration of the access system can comprise an extraction bag which is expanded by the effector portion of the at least one spreading element.

As described above, the access system according to the invention can have a fluid feed in the second embodiment, too.

Also proposed according to the invention is a method for assembling an access system for endoscopic operations, which comprises the following steps of
- providing a trocar having a trocar sleeve,
- providing a cover having a working duct,
- providing at least one spreading element having a retaining portion and an effector portion,
- providing an extraction bag,
- passing the effector portion of the at least one spreading element through the trocar sleeve and into the extraction bag,
- positioning the retaining portion of the at least one spreading element in the trocar,
- fitting the cover on the trocar such that its working duct extends through the trocar sleeve and the retaining portion of the at least one spreading element is clamped in place between the trocar and cover, and
- expanding the extraction bag by way of the at least one spreading element.

As also already described above, it is particularly advantageous in this method for a suitable number of spreading elements to be introducible successively into the access system and into the extraction bag. The expanded working region in the extraction bag only arises when the spreading element or spreading elements are held securely in the trocar.

It goes without saying that the abovementioned features are usable not only in the combination specified in each case but also in other combinations or on their own without departing from the scope of the present invention.

BRIEF DESCRIPTION OF THE DRAWINGS

The invention is explained and described in more detail in the following text by way of a number of selected exemplary embodiments in conjunction with the accompanying drawings, in which FIG. 5 shows a side view of a spreading element, FIG. 6 shows a side view of a spreading element.

DETAILED DESCRIPTION

Figure 1:
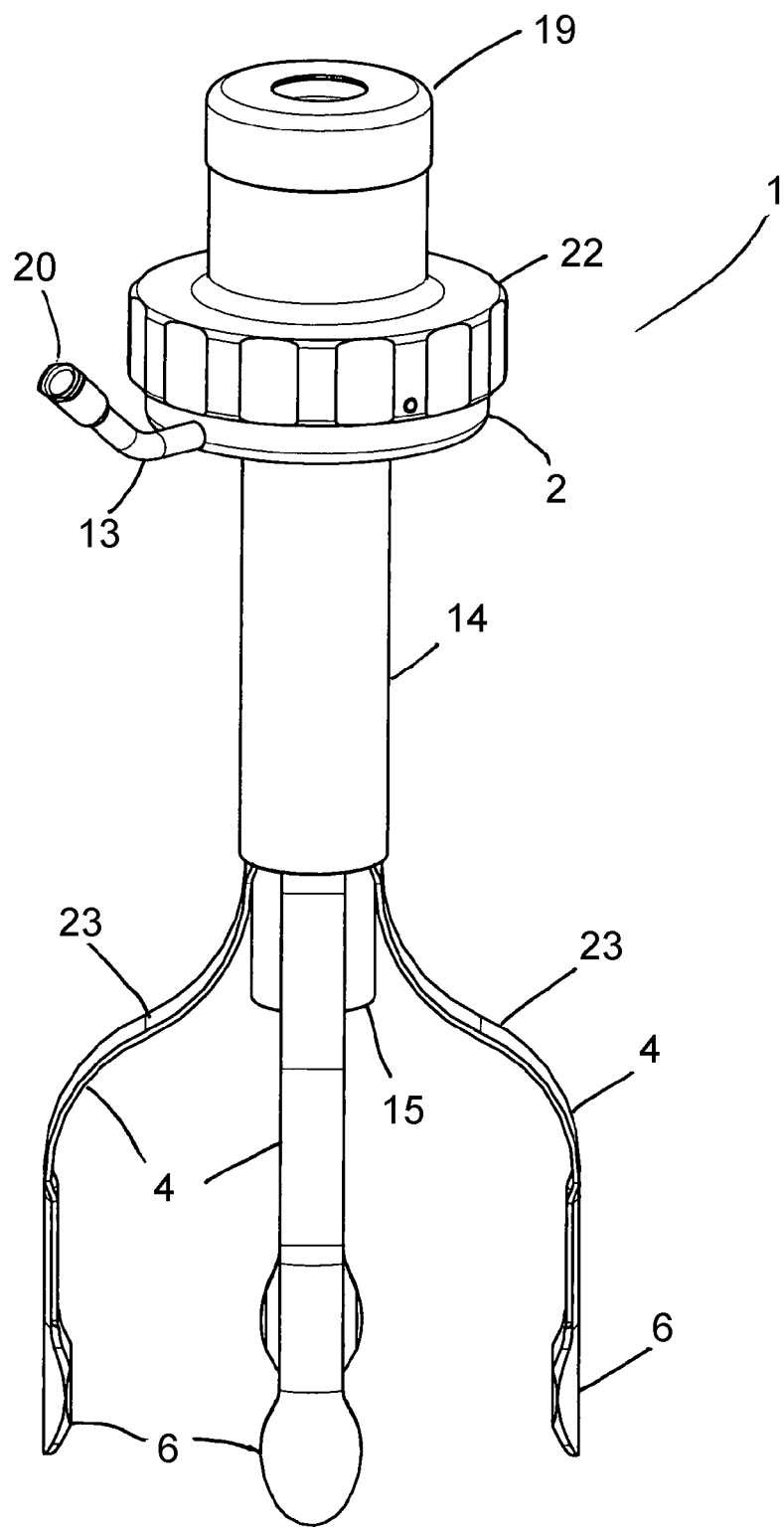
FIG. 1 shows a schematic perspective oblique view of the access system according to the invention in the assembled state.

The exemplary illustration in FIG. 1 shows a preferred exemplary embodiment of the access system 1 according to the invention for endoscopic operations in the assembled state. It consists of a trocar 2 having a trocar sleeve 14. It can additionally have a fluid feed 13, which is equipped for example with a Luer connector 20. The cover 3 of the access system 1 comprises a grip part 22 and a tubular working duct 15 which extends concentrically through the trocar sleeve 14 and is longer than the trocar sleeve 14 and therefore protrudes from the latter. Furthermore, the trocar system according to the invention includes a sealing cap 19 which allows the introduction of an instrument, for example a morcellator (not illustrated), but prevents gas from escaping from the body cavity or the extraction bag. In order to expand an extraction bag, use is made of four spreading elements 4, the effector portions 6 of which protrude between the trocar sleeve 14 and working duct 15. Their legs 23 are curved outwards in an approximately S-shaped manner such that the effector portions 6 of the spreading elements 4 lie on an imaginary circular cylindrical surface which lies concentrically around the trocar sleeve 14 and the working duct 15.

Figure 2:
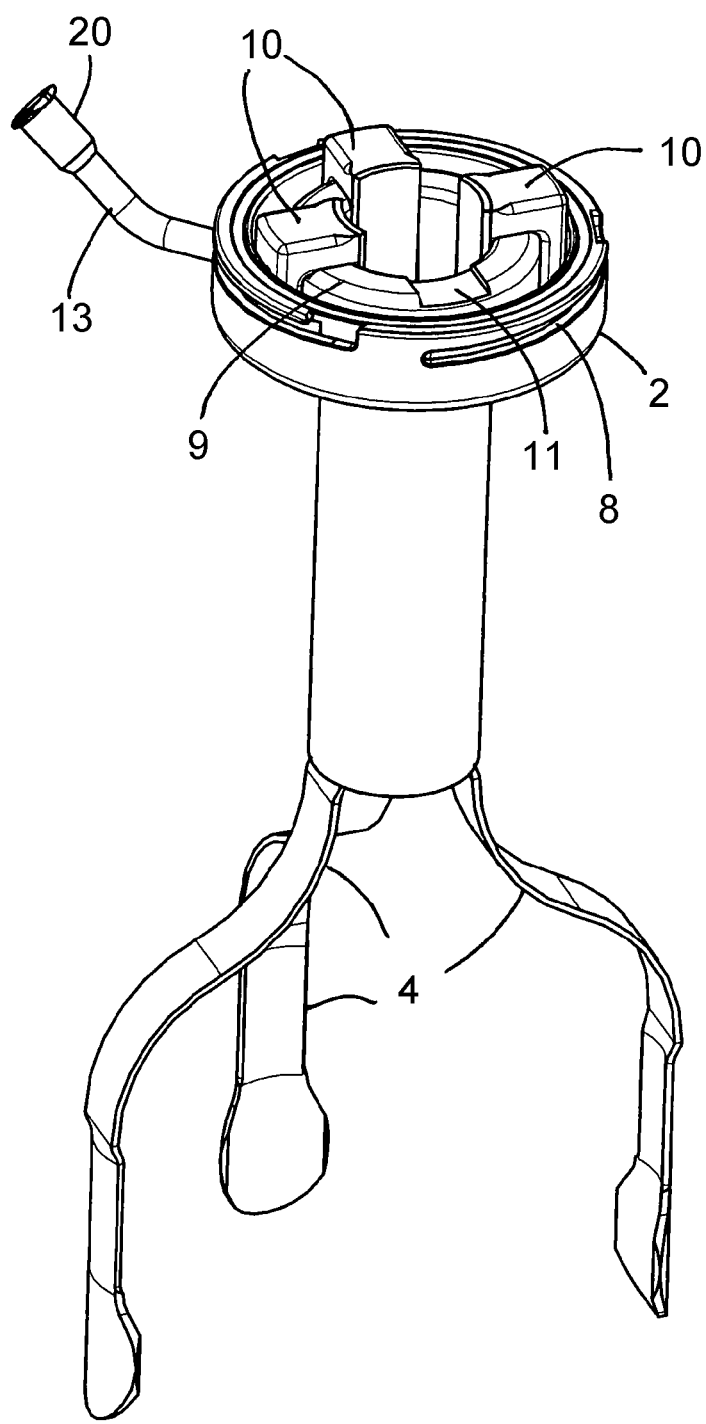
FIG. 2 shows a schematic perspective oblique view of the trocar with spreading elements.

FIG. 2 shows the trocar 2 with three inserted spreading elements 4 and without the cover 3. The grooves of the bayonet mount 8 are illustrated on the trocar 2. Furthermore, FIG. 2 shows the retaining ring 9 of the receiving region 8 having four positioning portions 11 (three concealed). Located on the retaining ring 9 in the set-back positioning portions 11 are the retaining clips 10 of the three fitted spreading elements 4.

Figure 3:
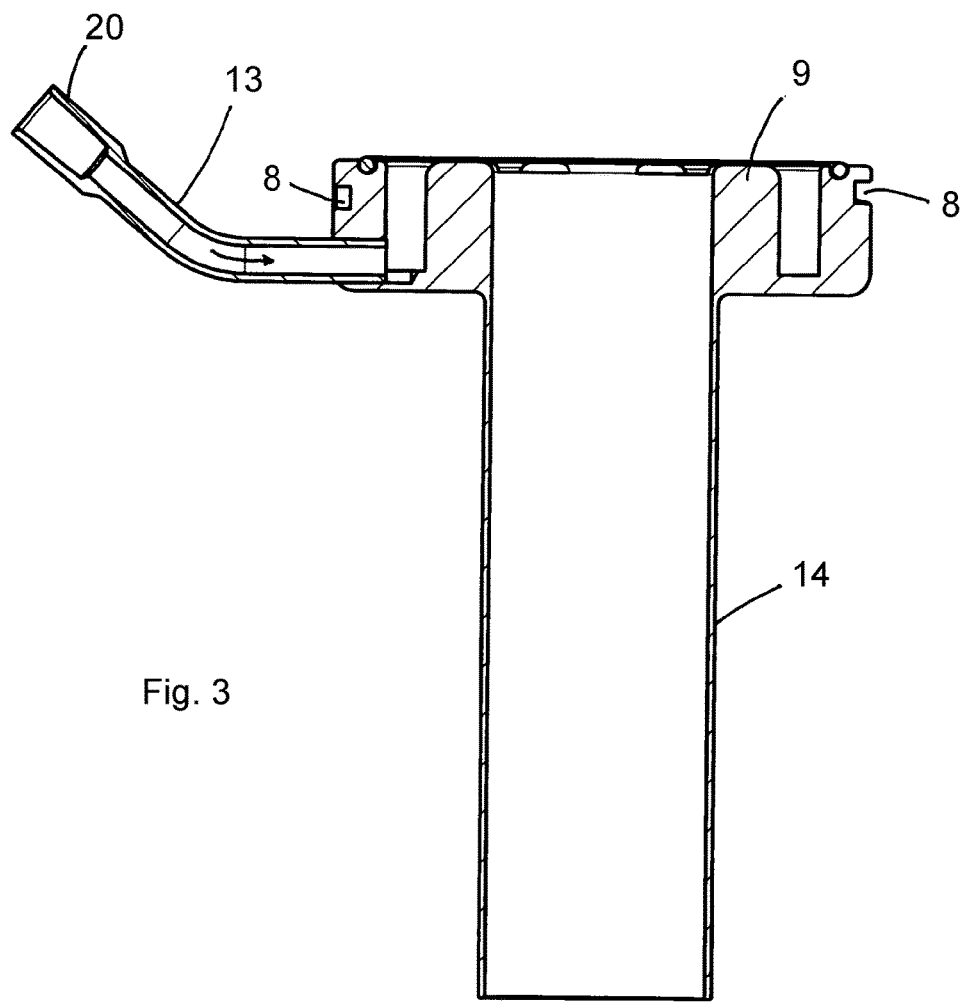
FIG. 3 shows a sectional illustration of the trocar.

FIG. 3 shows the trocar 2 with its trocar sleeve 14, the retaining ring 9, the slots of the bayonet mount 8 and the fluid feed 13.

Figure 4:
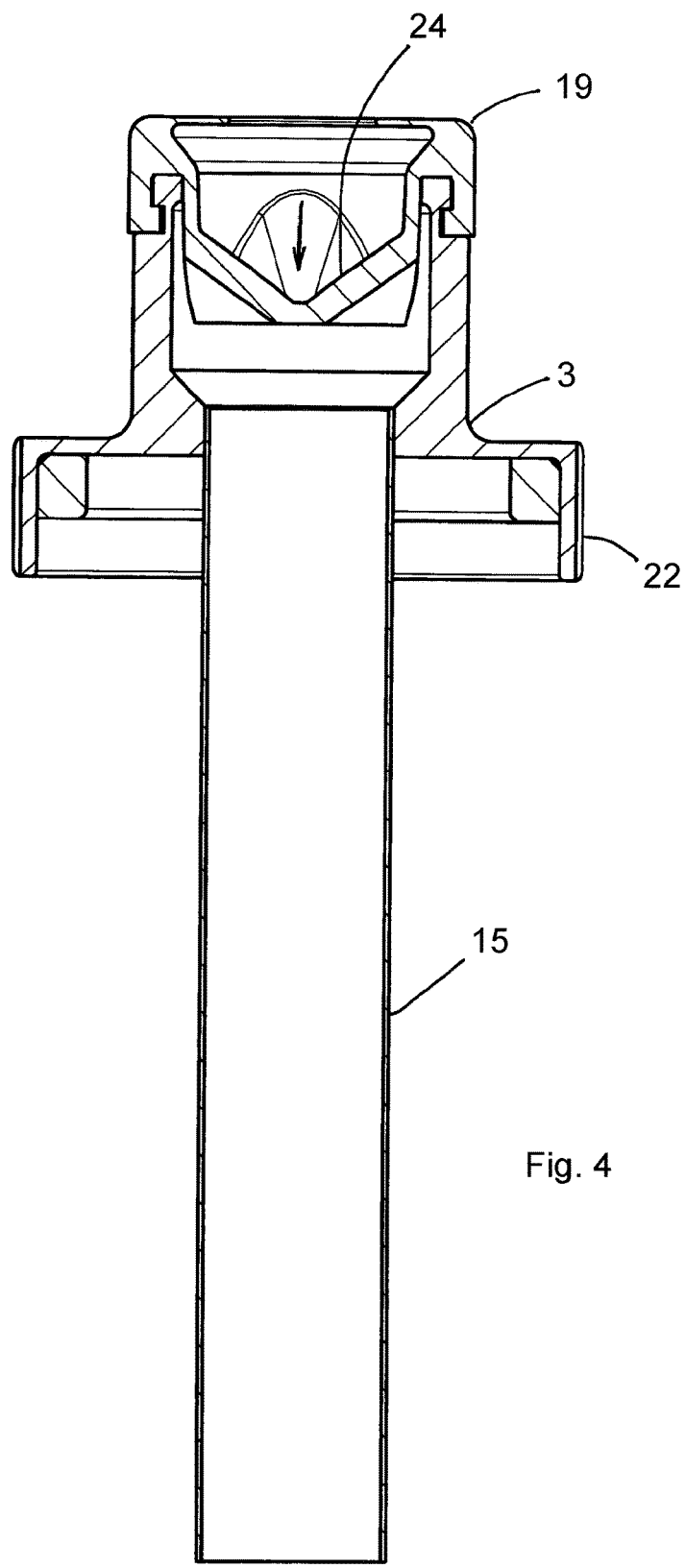
FIG. 4 shows a sectional illustration of the cover.

FIG. 4 shows the cover 3 with the grip part 22 and the working duct 15 with the sealing cap 19 in place thereon. The sealing cap 19 consists preferably of plastics material and can be a disposable product. Located in its interior are one or more valve flaps 24 which allow the introduction of an instrument but prevent gas from passing out in the opposite direction. The valve cap has protrusions which engage in corresponding recesses in the cover. Not illustrated are pins or protrusions which engage in the grooves of the bayonet mount 8 of the trocar 2.

FIGS. 5 and 6 show a spreading element 4 with its retaining portion 5, the retaining clip 10 and the effector portion 6. In FIG. 6, the contour 25, corresponding to a circular cylindrical jacket, of the retaining portion and of the effector portion is illustrated, said contour 25 being adapted to the intermediate space between the trocar sleeve 14 and working duct 15.

The invention claimed is:

1. An access system for endoscopic operations, comprising:
    a trocar;
    a cover that is fittable on the trocar; and
    at least one spreading element having a retaining portion and an effector portion;
    wherein the access system has, between the trocar and the cover in a fitted state, a receiving region for the retaining portion of the at least one spreading element; and
    wherein the access system comprises an extraction bag which is expanded by the effector portion of the at least one spreading element.

2. The access system according to claim 1, wherein the trocar and the cover have a bayonet mount for fitting.

3. The access system according to claim 1, wherein the receiving region comprises an annular retaining ring.

4. The access system according to claim 3, wherein the retaining portion of the at least one spreading element has a retaining clip adapted to the annular retaining ring.

5. The access system according to claim 4, wherein the annular retaining ring has at least one positioning portion adapted to the retaining clip of the at least one spreading element.

6. The access system according to claim 1, wherein the access system has 2 or 3 or 4 or 5 or 6 spreading elements.

7. The access system according to claim 1, wherein the trocar has a fluid feed.

8. An access system for endoscopic operations, consisting of:
- a trocar having a trocar sleeve;
- a cover that is fittable on the trocar and has a working duct and at least one spreading element;
- wherein the working duct extends concentrically within the trocar sleeve in a fitted state; and
- wherein the access system comprises an extraction bag which is expanded by an effector portion of the at least one spreading element.

9. The access system according to claim 8, wherein at least one portion of the at least one spreading element extends within an intermediate space between the trocar sleeve and working duct.

10. The access system according to claim 9, wherein the at least one spreading element has, at least in portions, a circular cylindrical contour which is adapted to a contour of the trocar sleeve and/or of the working duct.

11. The access system according to claim 8, wherein the access system has 2 or 3 or 4 or 5 or 6 spreading elements.

12. The access system according to claim 8, wherein the access system has a fluid feed.

13. A method for assembling an access system for endoscopic operations, comprising the steps of
- providing a trocar having a trocar sleeve;
- providing a cover having a working duct;
- providing at least one spreading element having a retaining portion and an effector portion;
- providing an extraction bag;
- passing the effector portion of the at least one spreading element through the trocar sleeve and into the extraction bag;
- positioning the retaining portion of the at least one spreading element in the trocar;
- fitting the cover on the trocar such that its working duct extends through the trocar sleeve and the retaining portion of the at least one spreading element is clamped in place between the trocar and cover; and
- expanding the extraction bag by way of the at least one spreading element.

* * * * *